United States Patent
Murray

(10) Patent No.: US 6,368,784 B1
(45) Date of Patent: *Apr. 9, 2002

(54) ELECTROPORATION BUFFER WITH CRYPROTECTIVE CAPABILITIES

(75) Inventor: James Hamer Murray, Cambridgeshire (GB)

(73) Assignee: Warner-Lambert Company, Morris Plains, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/402,591

(22) PCT Filed: Jul. 28, 1999

(86) PCT No.: PCT/US99/16978

§ 371 Date: Oct. 5, 1999

§ 102(e) Date: Oct. 5, 1999

(87) PCT Pub. No.: WO00/09732

PCT Pub. Date: Feb. 24, 2000

Related U.S. Application Data

(60) Provisional application No. 60/096,433, filed on Aug. 13, 1998.

(51) Int. Cl.$^7$ .............................. A01N 1/02; C12Q 1/68; C12P 21/06
(52) U.S. Cl. ........................... 435/1.3; 435/6; 435/69.1; 435/412; 435/413; 800/292; 800/279; 800/286
(58) Field of Search ............................. 435/1.3, 6, 69.1, 435/412, 413; 800/292, 279, 286

(56) References Cited

U.S. PATENT DOCUMENTS

| | | | |
|---|---|---|---|
| 5,470,568 A | 11/1995 | Lee | 424/78.02 |
| 5,911,223 A | 6/1999 | Weaver et al. | 128/898 |

FOREIGN PATENT DOCUMENTS

| | | | |
|---|---|---|---|
| SU | 1708835 | * | 1/1992 |

OTHER PUBLICATIONS

Sambrook et al., Molecular Cloning: A Laboratory Manual, 2d ed., (1989) Cold Spring Harbor Laboratory Press, Cold Spring Harbor, NY, pp. 1.74–1.81.*
Freshney, "Culture of Animal Cells: A Manual of Basic Techniques" (1987) Alan R. Liss, Inc., NY, pp. 215–225.*
Tsong, "Electroporation of cell membranes", *Biophys. J.*, vol. 60, 1991, pp. 297–306.
van den Hoff et al., "The osmolarity of the electroporation medium affects the transient expression of genes", *Nucleic Acids Res.*, vol. 18, No. 21, 1990, p. 6464.
van den Hoff et al., "Electroporation in 'introcellular' buffer increases cell survival", *Nucleic Acids Res.*, vol. 20, No. 11, 1992, p. 2902.
Tanaka et al., "Improved Electroporation efficiencies for COS–7 Cells using the Optimix Media Kit", *Pulse Times*.
Chernomordik et al., "The electrical breakdown of cell and lipid membranes: the similarity of phenomenologies", *Biochimica et Biophysica Acta*, vol. 902, 1987, pp. 360–373.
Melkonyan et al., "Electroporation efficiency in mammalian cells is increased by dimethyl sulfoxide (DMSO)", *Nucleic Acids Res.*, vol. 24, No. 21, 1996, pp. 4356–4357.
Rols et al., "Control by ATP and ADP of voltage–induced mammalian–cell–membrane permeabilization, gene transfer and resulting expression", *Eur. J. Biochem.*, vol. 254, 1998, pp. 382–388.
Golzio et al., "Control by Osmotic Pressure of Voltage–Induced Permeabilization and Gene Transfer in Mammalian Cells", *Biophys. J.*, vol. 74, 1998, pp. 3015–3022.
Gauss and Lieber, "DEAE–dextran enhances electroporation of mammalian cells", *Nucleic Acids Res.*, vol. 20, No. 24, 1992, pp. 6739–6740.
PCT International Search Report, PCT/US99/16978.
Ausubel et al., "Current Protocols in Molecular Biology", 1990, Wiley & Sons, New York, p. A.3F.6.
Berthier et al., "Efficient transformation of *Lactobacillus sake* by electroporation",*Microbiology*, vol. 142, 1996, pp. 1273–1279.
Baranov et al., "Incorporation of DNA into germ cells of male mice by electroporation and dimethylsulfoxide", *Tsitol. Genet.*, vol. 24, No. 3, 1990, pp. 3–7.
Lin et al., "Feasibility study of applying electroporation on the cryopreservation of oyster embryos and eggs", *Cryobiology*, vol. 33, No. 6, 1996, p. 644; Meeting info: 33$^{rd}$ Annual Meeting of the Society for Cryobiology, Indianapolis, IN, Aug. 17–21, 1996, abstract No. 59.

* cited by examiner

Primary Examiner—Karen Cochrane Carlson
Assistant Examiner—Stephen Tu
(74) Attorney, Agent, or Firm—Charles W. Ashbrook

(57) ABSTRACT

The instant invention is a novel buffer which enables simultaneous cryoprotection and transfection of mammalian cells. It enables the user to make cell stocks which can be kept long term. Use of these cell stocks circumvents the need to culture cells each time a transfection is undertaken. It alleviates the need for continuous cell culture and repeated transfections due to transfection variability.

20 Claims, No Drawings

ELECTROPORATION BUFFER WITH CRYPROTECTIVE CAPABILITIES

This application claims benefits of Provisional Application Ser. No. 60/096,433 filed Aug. 13, 1998.

BACKGROUND OF THE INVENTION

Transfection of mammalian cells is a procedure whereby a molecule is placed into a cell by passing it through the cell's outer membrane without perturbing the viability of the cell. Molecules such as DNA, RNA, and proteins are often the transfected material.

Generally, the transfectant will not passively pass through the intact cell membrane. Its passage is aided by transient disruption of the membrane. Four methods are in common use.

Gene gun wherein the transfectant is first bound to a solid particle such as graphite or gold and shot at high velocity into the cell.

Liposome mediated transfection wherein a liposome complex is formed between lipid and transfectant. The liposomes interact with the cell membrane facilitating the passage of the transfectant into the cell.

Calcium phosphate, that chelates DNA and form a precipitate that is internalised.

Electroporation mediated transfection wherein an electrical field pulse is applied across the cell membrane which causes transient pore formation in the cell membrane. This enables the transfecting molecule to pass through the pore into the cell.

A prerequisite for all the above methods is that sufficient cells are present for transfection. This is achieved by prior expansion of cells by culture. The Gene gun is not usually a method of choice, as it is inefficient and requires that the cells are grown adhered to a surface. Liposome and electroporation mediated transfection are more efficient than the Gene gun. Liposome mediated transfection has been more popular than electroporation mediated transfection. This is partly due to the fact that liposome mediated transfection can be carried out on cells growing in solution and cells grown adhered to a surface. Electroporation mediated transfection is more efficient than liposome mediated transfection and is generally carried out on cells grown in solution. With the advent of electrophorus membranes (e.g., Corning) which allow electroporation of adherently grown cells, this imbalance is likely to be redressed. In both instances, standard cell culture media is a poor media for transfection. Therefore, culture media must be replaced with a suitable transfection solution prior to transfection.

The majority of cultured cells used in industry and academia are used for transient or stable (permanent integration of the transfected molecule) transfection studies. These cells lines are available through organizations such as the ETACC and ATCC. Cells lines are obtained as a frozen aliquot and clonally expanded by the purchaser. Once expanded, the cells are generally kept as a growing culture and as a frozen stock. This growing culture is the source of cells for transfection. Cells are generally frozen in a cocktail of enriched culture media and cryoprotectant. The most common cryoprotectant used is dimethyl sulfoxide (DMSO). However, glycerol, sucrose, trahalose and proline and others are sometimes used. Cryoprotectants are thought to aid cell survival by preventing ice nucleation in cells, which is a contributory factor to cell rupture upon freezing, while the culture media provides nutrients. The multiple factors involved in successful cryo-preservation of Animal cells have been extensively reviewed by Doyle et. al. 1988.

The generally used procedure for transfection is as follows:
(1) Culture cells to produce sufficient cells for transfection. This step can take several days.
(2) Transfect cells.
(3) Study transfected cells.

The disadvantages of this procedure is that pre-culture of cells for transfection requires an excessive amount of time and resources. Moreover, the requirement for transfection to be repeated each time an experiment is undertaken may lead to variability in transfection.

SUMMARY OF THE INVENTION

The instant invention is a cryoprotectant for electroporation ready cells comprising molecules that protect cells during the freeze thaw cycle prior to electroporation.

It is a high efficiency electroporation buffer containing antioxidants and other critical molecules that help in the regeneration process after electroporation.

The cryoprotectant/electroporation buffer comprises the cold protection of culture media with cryoprotectant and the transfection capabilities of electroporation media.

The dual purpose buffer combines a cell-freezing medium and a high efficiency mammalian cell transfection buffer.

The buffer is selected from a range of cryoprotectants as described in Stacey, 1997, Stange & Mitzner, 1996, Grout et al 1990 & Doyle et al 1988, that include DMSO, glycerol, sucrose, trehalose, and protein.

Preferred buffer is DMSO, glycerol or sucrose.

The buffer is useful simultaneously and directly as a high efficiency electroporation transfection buffer and as a buffer to freeze cells for long-term storage.

The invention is further a method of buffering transfected material comprising:
a) freezing the material in electroporation/cryoprotection media,
b) resuspending the material in water,
c) resuscitating by defrosting at room temperature for about 1 minute and then 37° C. for ~2 minutes, depending on cell type and apparatus available.
d) mixing an aliquot of material with cells and placing them in an electroporation cell followed by transfecting the material in a culture dish In the invention, Cytomix, an intracellular ionic strength- and pH-mimicking buffer composed of 120 mM KCl; 0.15 mM $CaCl_2$; 10 mM $K_2HPO_4/KH_2PO_4$, pH 7.6; 25 mM Hepes, pH 7.6; 2 mM EGTA, pH 7.6; and 5 mM $MgCl_2$; pH adjusted with KOH, with added water and DMSO to final volume is resuspended and aliquoted into cryovials, wrapped and frozen to –20° C. over ~5 hours and then –70° C. overnight, deep freezing in nitrogen for ~5 days wherein the latter stage of freezing depends on the sophistication of the available apparatus and has an impact on the successful preservation.

DETAILED DESCRIPTION OF THE INVENTION

The instant invention eliminates the need for repetitive pre-culture and therefore has the following advantages over the art. Experiments are initiated at the transfection step, significantly reducing the time and resources required greatly. The number of experimental steps is reduced and so is the likelihood of infection of cells. With all of the transfected cells from the same stock, there is a reduction of intra- and inter-experimental variation. This invention allows one to do a different experiment each day; one is not confined to one available batch.

In the instant invention, the need to pre-culture cells prior to transfection is eliminated by producing a frozen cell stock. This cell stock has the following characteristics: each aliquot has sufficient cells for a transfection; cells are viable when resuscitated; and cells are capable of immediate transfection upon resuscitation. The transfection technique used is already established, e.g., liposome transfection or electroporation. For each aliquot to have sufficient cells for a transfection, cells must first be cultured in sufficient quantities for stocks to be made. For the cells to be viable when resuscitated and be capable of immediate transfection upon resuscitation, a buffer which has a dual function is required. The buffer must function as a cryoprotectant and a transfection buffer. This buffer is the object of the instant invention.

The invention is a cryoprotectant/electroporation buffer useful simultaneously and directly as a high efficiency electroporation transfection buffer and as a buffer to freeze cells for long-term storage. This is achieved by combining the cold protection of culture media with cryoprotectant and the transfection capabilities of electroporation media. This alleviates the need for continuous cell culture and repeated transfections due to transfection variability of current methods.

Cytomix (Knight & Scrutton 1986) also sold as Optimix (marketed by EquiBio) is an intracellular ionic strength mimicking buffer. This buffer protects against osmotic rupture as it has the same osmotic strength as the cell contents. It also contains additional salts and other critical molecules, including antioxidants that help in the regeneration process during and following destabilization caused by the electrical discharge through the cell (Tsong 1991). Cytomix has the following composition; 120 mM KCl, 0.15 mM $CaCl_2$; 10 mM $K_2HPO_4/KH_2PO_4$, pH 7.6; 25 mM Hepes, pH 7.6; 2 mM EGTA, pH 7.6; 5 mM $MgCl_2$; pH adjusted with KOH with ATP (pH 7.6 adjusted with KOH 2 mM) and Glutathione (5 mM) added just before electroporation (Van den Hoff et al., *Nucleic Acid Research,* 2902 Vol 20 No. 11 and Knight D. E. and Scrutton M. C., *Biochem J.,* 1986;234:497–506). This buffer offers good transfection efficiency and is thought to prevent leakage of the cytoplasmic components, protect membranes against oxidation, and facilitate resealing of pores. However, it does not offer good protection for freezing of mammalian cells.

Dimethyl Sulfoxide is used as a model cryoprotectant. Addition of DMSO to the above electroporation buffer results in a novel dual purpose buffer which is used directly as a cell freezing buffer and a high efficiency electroporation transfection buffer.

A detailed protocol follows. The salient points of the experiment are outlined below.
(1) Cos-7 cells were cultured in media consisting of DMEM (500 ml Gibco Cat. No. 31966-021), FBS (50 ml Gibco Cat No. 10100-0155) and pen/strep (5 ml Gibco Cat No. 15070-022) at 37° C. according to protocol in 6×T175 flasks until 70–80% confluent.
(2) Cos-7 cells were detached from the flask with trypsin (Gibco Cat. No. 45300-019) and peletted at 200 g for 5 minutes at room temperature. Cells were washed twice in 50 ml of Optimem-1 (Gibco Cat. No. 51985-026) at room temperature then resuspended in EquiBio buffer A (cytomix buffer-ATP-Glutathione).
(3) Cos-7 cells were split into two aliquots of $10 \times 10^6$ cells and half transformed immediately and half frozen in 2×0.7 ml aliquots.
(4) To EquiBio buffer B (2×cytomix buffer) was added ATP and Glutathione. Cells ($10 \times 10^6$) was resuspended in a solution of 800 $\mu$l of the above with 800 $\mu$l of $H_2O$ with (60 $\mu$g of pGL3-Control, encoding luciferase gene) according to the protocol and 800 $\mu$l placed in a 4 mm electroporation cell (Flowgen E5-0100).
(5) Cells were immediately transformed at 250V, 1050 $\mu$F, and infinite resistance.
(6) An aliquot (50 $\mu$L) was plated out in 6-well plates and cultured overnight.
(7) Cos-7 cells were harvested in a similar manner to above and luciferase activity measured.
(8) The remaining Cos-7 cells were frozen in electroporation/cryoprotection media as follows:
To 2×Optimix (above) was added $H_2O$ and 5% DMSO (75 $\mu$L) to a final volume of 1400 $\mu$L. Cells ($10 \times 10^6$) were resuspended in the above and 2×0.7 ml was aliquoted into cryovials. Cells were wrapped in cotton wool and frozen to −20° C. over a time period of about 5 hours and then −70° C. overnight. Cells were deep frozen in liquid nitrogen for 5 days.
(9) DNA (60 $\mu$g) was resuspended in 200 $\mu$l of $H_2O$.
(10) Frozen Cos-7 cells were resuscitated by defrosting at room temperature for 1 minute and then 37° C. for 2 minutes.
(11) A 100 $\mu$l aliquot of DNA was quickly mixed with cells (700 $\mu$l) and then placed in an electroporation cell. Cells were transfected as above in 6-well culture dish.

Cells were observed 1 hour and 18 to 24 hours after transfection. In both cases, transfected cells had a similar morphology and bedded down on the culture plates in a similar manner.

Luciferase activity was measured 18 to 24 hours after transfection as described above. Luciferase activity of non-frozen Cos-7:
(1) 586.2
(2) 582.8
(3) 591.8
(4) 573.8
(5) 559.4
(6) 572.3 Average=577.7

| Luciferase activity of frozen Cos-7: | | | | | |
|---|---|---|---|---|---|
| (1) | 210.8 | (7) | 215.9 | (13) | 195.8 |
| (2) | 212.6 | (8) | 214.7 | (14) | 199.0 |
| (3) | 210.8 | (9) | 215.7 | (15) | 199.4 |
| (4) | 198.3 | (10) | 196.3 | (16) | 225.6 |
| (5) | 300.9 | (11) | 199.9 | (17) | 231.8 |
| (6) | 199.1 | (12) | 201.8 | (18) | 230.4 Average = 214.4 |

These results show that cells frozen in electroporation/cryoprotection buffer are capable of being viable after being frozen in liquid nitrogen and are capable of being transfected by electroporation. The non-frozen cells are more electrporationally competent than the frozen cells due to several possible factors: Not all cells that are frozen are viable and addition of DMSO possibly reducing the electroporation efficiency of the buffer.

A comparison of luciferase activity in the non-frozen and frozen transfected cells indicated that frozen cells and non-frozen cells have luciferase activity. This shows that both cell types have been transfected. Previous studies indicated that non-transfected cells do not have luciferase activity.

Non-frozen cells have three times more luciferase activity than frozen cells. This indicates that there was less luciferase activity in the frozen cells. This could be due to less viable cells present after resuscitation for transfection or to a decrease in the electroporation efficiency. An active method of cell freezing coupled to cryoprotection optimization will improve transfection efficiency.

Cell culture, harvesting, transfection, luciferase activity measurements and cell freezing were standard laboratory techniques. With regards to cell freezing, the method used was determined by the availability of equipment. A more sophisticated active method would produce a higher titre of viable cells (see *Upstream Processes: Equipment and Techniques,* 1988; Doyle A. et al., *Cryopreservation of Animal Cells,* 19:1–17). The protocol for cell resuscitation was generally known. Other more sophisticated protocols can be used.

For efficient transfection, it is important to have a solution of transfectant in this example DNA. The DNA was dissolved in water, but transfectants can be resuspended in most solution which allows solubilization.

EXAMPLE 1

(1) Cos-7 cells were cultured to produce sufficient cells for immediate transfection and for production of frozen cell stocks. These cells were detached from the flask (Steps 1 to 2 above).

(2) A plasmid pGL3-Control (Promega) which encodes a promoter and structural gene for luciferase was used as a marker of transfection efficiency.

(3) Cos-7 cells aliquots ($5 \times 10^6$) was resuspended to a final volume of 800 µl of Optimix/$H_2O$ with 30 µg of pGL3-Control (400 µl of 2×Optimix, 300 µl of $H_2O$, 100 µl of DNA) and the cells transfected by electroporation. A sample was cultured in growth media. Twenty-four hours posttransfection luciferase activity was measured. It was assumed that the greater the amount of luciferase present, the more efficient the transfection (Steps 4 to 7 above).

(4) Remaining aliquots of Cos-7 cells were resuspended in 700 µl of modified buffer (400 µl of 2×Optimix, 265 µl of $H_2O$, 35 µl of DMSO (5% final)). These cells were then frozen (Steps 3 and 8 above; see below for Cryopreservation of Animal Cell Lines).

(5) Frozen Cos-7 cells were resuscitated, 100 µl of DNA solution added and the cells transfected by electroporation as above (Steps 9 to 11 above).

(6) An aliquot of transfected cells was cultured in a similar manner to above and the luciferase activity measured. The electroporation apparatus is available through Flowgen, Lynn Lane, Shenstone, Lichfield, Staffs WS14 OEE:

| | |
|---|---|
| EasyJect plus | E5-0310 |
| "in-situ" chamber electroporation cell | E5-0204 |
| 4 mm cuvettes | E5-0100 |
| Adherent cell electroporation cuvettes | B5-0200 |
| Adherent cells electroporation cell | E5-0208. |

EXAMPLE 2
Cryopreservation of Animal Cell Lines

To ensure the continuation of supply of a cell line, it is necessary to provide adequate stocks of cryopreserved cells. The following is a guide to successful cryopteservation. First consider the method of freezing. The most reliable method is to use a controlled rate freezer. There are two types, i.e., active and passive. The former is electronically controlled to cool at a pre-set rate using liquid nitrogen, i.e., programmable. Passive freezers either rely on holding cells at a predetermined temperature, e.g., $-25°$ C. for a certain time period prior to plunging them into liquid nitrogen, or a more recent type uses a pre-cooled block which cools the cells at $-1°$ C./minute to around $-150°$ C. The often used, but not always reliable, method of placing ampoules in $-80°$ C. freezers insulated in a polystyrene box is not strongly recommended. Although many laboratories use this method routinely, the inventors have found cell viability rarely exceeds 75%. Controlled rate freezers will normally preserve cells at the original viability.

Cells for cryopreservation should be prepared as follows:
Only freeze cells from cultures actively growing, i.e., in the log phase of growth. They must be intact and healthy and preferably grown in antibiotic free medium. Test for mycoplasma and microbial contaminants whenever possible.

Allow between 4 to $10 \times 10e6$ viable cells per ampoule. Fewer cells than this may give problems in establishing cultures after resuscitation, and a greater number can cause a decrease in viability.

Prepare a freezing medium either from the growth medium with 20% Serum to which 7% to 9% (v/v) sterile dimethyl sulphoxide (DMSO) or glycerol is added, or whole serum with 9% cryoprotectant. The latter freezing medium gives better protection against pH changes as most culture media contain bicarbonate and become alkaline on exposure to air. Allow 1 ml per ampoule.

Prepare cells in the same manner as for routine subcultures, and then pellet in sterile 15 to 250 ml conical tubes at 70 to 100×g. If trypsin is used, it must be neutralized by addition of serum containing medium to the cells prior to centrifugation. At least 1 ml of serum is needed for each milliliter of trypsin used.

Decant the medium fully and resuspend the cell pellet(s) in the required volume of freezing medium. Ensure a homogeneous mixture by gentle agitation. Distribute the cells into sterile plastic screw-top cryotubes, i.e., 1 mL/tube. The cryotubes must be clearly marked with a permanent marking pen. The cells should then immediately be cooled at a rate of between 1 to $-5°$ C./minute. The ECACC currently uses $3°$ C./minute. Once ampoules reach $-60°$ C., the rate of cooling can be increased if desired. After freezing, ampoules must be transferred to a nitrogen storage vessel and either held in gas or liquid phase nitrogen. A temperature of $-80°$ C. to $-100°$ C. is only useful for short-term storage, i.e., weeks or months. It is recommended that cells are passaged no more than 30 times before starting from a new ampoule. Prepare a seed stock of 5 to 10 ampoules and from one of these prepare your working stock.

EXAMPLE 3
Resuscitation of Frozen Cells

After storage in nitrogen, ampoules may explode if not handled correctly. During their retrieval from storage and subsequent thawing, personnel must wear full protective clothing, i.e., full face shield, insulated gloves, and lab coat.

Remove the ampoule(s) from storage and unscrew the cap ¼ turn to release any residual nitrogen. Place the ampoules in a rack and leave in a sterile flow cabinet for 1 to 2 minutes or until all gas has escaped. Tighten the caps and place the rack in a water bath at the normal growing temperature of the cells, e.g., $25°$ C. for insect lines, $37°$ C. for mammalian lines. The ampoules should not be submerged so that water does not enter the ampoule and contaminate the cells. A piece of floating foam with holes makes an ideal rack. The water bath should have clean water containing an antimicrobial agent.

Once the ampoules have fully thawed, transfer to a class R cabinet and wipe with 70% alcohol.

Transfer the ampoule contents either directly into a prepared culture flask or into a 15 ml centrifuge tube to remove the cryoprotectant. Slowly add 10 ml of growth medium to the tube, mix, and centrifuge at the lowest speed required to pellet the cells, e.g., 70 to 100×g.

Decant the supernatant from pelleted cells and re-suspend in fresh medium. Transfer the cells to a culture flask. To ensure a rapid recovery, it is recommended that cells should be seeded at between ½ to ¼ their maximum density. In practice, the maximum density of many suspension lines is 10e6/ml and for attached lines between 1 to 3×10e5 cells/cm$^2$. The figures refer to viable cells, which can be assessed using trypan blue stain (Liss A. R., *Cryopreservation of Animal Cells in Advances in Biotechnological Processes*, 1988;7:1–17).

In the above examples, the amounts of cryoprotectant added to the electroporation buffer can vary from 0 to 40% depending on the cell type. The amount of cells added to the electroporation/cryoprotectant buffer prior to freezing is determined by cell type. The amount of DNA added to the electroporation/cryoprotectant buffer can vary but in the case above was 30 ug.

What is claimed is:

1. A dual-purpose cryoprotectant/electroporation buffer for mammalian cells consisting of a cryoprotectant and an electroporation buffer, wherein the electroporation buffer consists of an intracellular ionic strength- and pH-mimicking buffer and from 0 to 3 agents selected from the group consisting of an anti-oxidant, a phosphorylated nucleotide, and water.

2. A dual-purpose buffer according to claim 1 consisting of a cryoprotectant and an electroporation buffer which is an intracellular ionic strength- and pH-mimicking buffer.

3. A dual-purpose buffer according to claim 1 wherein the cryoprotectant is selected from dimethylsulfoxide (DMSO), glycerol, sucrose, trehalose, and protein.

4. A dual-purpose buffer according to claim 1 wherein the cryoprotectant is selected from DMSO, glycerol, and sucrose.

5. The dual-purpose buffer according to claim 1, wherein the electroporation buffer consists of an intracellular ionic strength- and pH-mimicking buffer, an anti-oxidant, and a phosphorylated nucleotide.

6. The dual-purpose buffer according to claim 5, wherein the anti-oxidant is glutathione and the phosphorylated nucleotide is ATP.

7. A dual-purpose buffer according to claim 1 wherein the electroporation buffer includes about 120 mM KCl; about 0.15 mM CaCl$_2$; about 10 mM K$_2$HPO$_4$/KH$_2$PO$_4$, pH 7.6; about 25 mM Hepes, pH 7.6; about 2 mM EGTA, pH 7.6; and about 5 mM MgCl$_2$; (pH adjusted with KOH).

8. A dual-purpose buffer according to claim 1 wherein the electroporation buffer includes about 120 mM KCl; about 0.15 mM CaCl$_2$; about 10 mM K$_2$HPO$_4$/KH$_2$PO$_4$, pH 7.6; about 25 mM Hepes, pH 7.6; about 2 mM EGTA, pH 7.6; and about 5 mM MgCl$_2$; (pH adjusted with KOH; water; and DMSO.

9. A dual-purpose buffer according to claim 1 wherein the electroporation buffer includes about 120 mM KCl; about 0.15 mM CaCl$_2$; about 10 mM K$_2$HPO$_4$/KH$_2$PO$_4$, pH 7.6; about 25 mM Hepes, pH 7.6; about 2 mM EGTA, pH 7.6; and about 5 mM MgCl$_2$; (pH adjusted with KOH); glutathione; and ATP.

10. A dual-purpose buffer according to claim 1 wherein the cryoprotectant is DMSO.

11. A dual-purpose buffer according to claim 1 wherein the cryoprotectant is DMSO at a concentration of about 5 percent volume/volume.

12. A dual-purpose buffer according to claim 1 wherein the cryoprotectant is glycerol.

13. A dual-purpose buffer according to claim 1 wherein the anti-oxidant is glutathione.

14. A dual-purpose buffer according to claim 1 wherein the anti-oxidant is glutathione at a concentration of about 5 mM.

15. A dual-purpose buffer according to claim 1 wherein the phosphorylated nucleotide is ADP or ATP.

16. A dual-purpose buffer according to claim 1 which is useful simultaneously and directly as a high efficiency electroporation transfection buffer and as a buffer to freeze cells for long-term storage.

17. A method of transfecting mammalian cells that have been frozen in electroporation-ready form in the dual-purpose buffer according to claim 1, comprising:
   a) resuscitating the frozen electroporation-ready cells by defrosting;
   b) adding a material to be transfected;
   c) transfecting the cells produced in Step a) by electroporation; and
   d) culturing the transfected cells produced in Step c) in a culture medium.

18. A method of transfecting mammalian cells comprising:
   a) freezing the cells in the dual-purpose buffer according to claim 1,
   b) resuspending material for transfection in water,
   c) resuscitating the cells produced in Step a) by defrosting at room temperature for about 1 minute and then at 37° C. for ~2 minutes, depending on cell type and apparatus available, and
   d) mixing an aliquot of the resuspended material produced in Step b) with the resuscitated cells produced in Step c), and placing the mixture in an electroporation cell followed by transfecting the material in a culture dish.

19. A method according to claim 18 wherein Step a) comprises suspending the cells in an intracellular ionic strength- and pH-mimicking buffer composed of about 120 mM KCl; about 0.15 mM CaCl$_2$; about 10 mM K$_2$HPO$_4$/KH$_2$PO$_4$, pH 7.6; about 25 mM Hepes, pH 7.6; about 2 mM EGTA, pH 7.6; and about 5 mM MgCl$_2$; (pH adjusted with KOH), with added water and DMSO to final volume, and aliquoting the resulting suspension into cryovials, wrapping the cryovials, and cooling to −20° C. over ~5 hours and then −70° C. overnight, and then deep freezing in nitrogen for ~5 days wherein the latter stage of freezing depends on the sophistication of the available apparatus and has an impact on the successful preservation.

20. A method of storing mammalian cells in electroporation-ready form, comprising:
   a) harvesting the cells;
   b) suspending the cells produced in Step a) in a dual-purpose cryoprotectant/electroporation buffer for mammalian cells consisting of a cryoprotectant and an electroporation buffer, wherein the electroporation buffer consists of an intracellular ionic strength- and pH-mimicking buffer and from 0 to 3 agents selected from the group consisting of an anti-oxidant, a phosphorylated nucleotide, and water; and
   c) freezing the suspended cells produced in Step b).

* * * * *